(12) United States Patent
Duggal et al.

(10) Patent No.: US 11,033,352 B2
(45) Date of Patent: *Jun. 15, 2021

(54) ILLUMINATING SURGICAL DEVICE AND CONTROL ELEMENT

(71) Applicant: Illumix Surgical Canada Inc., Bright's Grove (CA)

(72) Inventors: Anil Duggal, Lexington, KY (US);
Paul Dobrovolskis, Ancaster (CA);
Roel H Kusters, Sittard (NL); Edsger Constant Pieter Smits, Eindhoven (NL); Stephan Harkema, Eindhoven (NL)

(73) Assignee: Illumix Surgical Canada Inc., Bright's Grove (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/199,159

(22) Filed: Nov. 24, 2018

(65) Prior Publication Data

US 2020/0030052 A1 Jan. 30, 2020

Related U.S. Application Data

(63) Continuation of application No. 15/203,552, filed on Jul. 6, 2016, now Pat. No. 10,213,271.

(51) Int. Cl.
*A61B 90/30* (2016.01)
*A61B 17/02* (2006.01)

(52) U.S. Cl.
CPC .............. *A61B 90/30* (2016.02); *A61B 17/02* (2013.01); *A61B 2090/309* (2016.02)

(58) Field of Classification Search
CPC ...................................................... A61B 90/30
See application file for complete search history.

(56) References Cited

U.S. PATENT DOCUMENTS

| | | | | |
|---|---|---|---|---|
| 8,511,847 B2 * | 8/2013 | Sharrah | ............... | F21V 21/0808 362/199 |
| 9,622,682 B2 * | 4/2017 | Chin | .................... | A61B 1/0638 |
| 9,730,685 B2 * | 8/2017 | Wan | ..................... | A61B 1/0684 |

* cited by examiner

*Primary Examiner* — Andrew Yang
(74) *Attorney, Agent, or Firm* — Soody Tronson; STLG Law Firm

(57) ABSTRACT

Embodiments of claimed subject matter are directed to an illuminating surgical device comprising a single control element to control an array of illuminating elements and an array of louvers to direct light from the individual illuminating elements toward a surgical field.

10 Claims, 4 Drawing Sheets

ILLUMINATING SURGICAL DEVICE AND CONTROL ELEMENT

BACKGROUND

1. Field

This disclosure relates generally to the field of surgical devices and, more particularly, to one or more approaches toward controlling illumination of a surgical device to illuminate a surgical area of interest.

2. Information

While performing a surgical procedure, a surgeon may utilize a retractor, which may permit the surgeon to draw lateral and deep layers of tissue away from underlying features. Responsive to the drawing or retracting of lateral and deep layers away from underlying features, a surgeon may focus his or her attention on, for example, repair, manipulation, and/or replacement of body organs, and other anatomical structures including, but not limited to, soft tissue, nerve, venous, arterial, tendinous, and bony structures, and/or may perform numerous other surgical procedures.

However, at times, a surgical instrument may bring about shadowing of light from an overhead source that is intended to illuminate a surgical area of interest. Additionally, other sources of blockage of overhead light may include the surgeon's head, body, and/or hands, for example, and/or one or more body parts of an assistant. Further, other instrumentation in and around the surgical field may obscure the surgical field from the surgeon's view. Accordingly, a surgeon may be required to reposition surgical instruments or overhead lighting or may be required to wear a headlamp so as to provide a clear, illuminated view of a surgical area of interest.

In many instances, light from an overhead source may be tightly directed toward an area of interest. However, since there may be a large distance between surgical instruments and an overhead light source, directed light may introduce optical artifacts, such as shadowing and glare on specific surfaces, which may reduce the visual quality of the illuminating area. Thus, the surgeon may reposition the surgical instrument or shift his or her position in a manner that reduces and/or avoids glare from overhead light sources. Accordingly, virtually any object that is between the light source and the surgical area being viewed may diminish the light in the surgical field hindering the ability of the medical personnel to visualize the important areas.

SUMMARY OF DISCLOSURE

Briefly, particular implementations may be directed to an illuminating surgical device comprising a substantially two-dimensional array of illuminating elements, which may function or operate to direct light towards a surgical field. In an embodiment, a single control element of the illuminating surgical device may be utilized to control the intensity of light from the two-dimensional array of illuminating elements and to control the placement of the illuminated surgical field. In an embodiment, a single control element of an illuminating surgical device may be movable along a first axis to control the direction of light from the two-dimensional array of illuminating elements parallel to the first axis. In an embodiment, the single control element of an illuminating surgical device may be movable along a second axis to control the direction of light from the two-dimensional array of illuminating elements parallel to the second axis. In an embodiment, a single control element of an illuminating surgical device may be movable along a third axis to control intensity of light from the two-dimensional array of illuminating elements, the third axis may be substantially perpendicular to the first axis and the second axis. In an embodiment, movement of a single control element of an illuminating surgical device may operate to control a plurality of louvers, the louvers may be operable to control the direction of the light from the two-dimensional array of illuminating elements. In an embodiment, depressing the single control element of the illuminating surgical device may function to bring about a change in intensity of light from the two-dimensional array of illuminating elements. In an embodiment, depressing of the single control element name bring about at least one step, of a plurality of steps, in the intensity of light from the two-dimensional array of illuminating elements.

In embodiments, an illuminating surgical device may comprise a circuit to extinguish the illuminating surgical device based, at least in part, on inactivity of the device over a duration. Illuminating elements of an illuminating surgical device may comprise organic light-emitting diodes.

In an embodiment, a surgical retraction device may comprise an illumination layer to accommodate an array of illuminating elements to generate light to be directed toward a surgical area. The surgical retraction device may further comprise a control layer to modify the placement of an illuminated surgical area relative to the array of illuminating elements or to modify the intensity of light from the array of illuminating elements, or to control a combination thereof, using a single control element. In an embodiment, a surgical retraction device may comprise a two-dimensional array of illuminating elements. In an embodiment, a single control element of a surgical retraction device may be moved along a first axis to control the direction of light from the array of illuminating elements parallel to the first axis. In an embodiment, the single control element may be moved along the second axis to control a direction of light from the array of illuminating elements parallel to the second axis. In an embodiment, the single control element of the surgical retraction device may be moved along the third axis to control it the intensity of light from an array of illuminating elements. In an embodiment, a single control element of the surgical retraction device may control intensity of light from the array of illuminating elements in a series of discrete steps.

In an embodiment, a surgical retraction device may comprise means for illuminating the surgical area, means for controlling placement of the illuminated surgical area along a first axis and a second axis, the first and the second axis to be substantially perpendicular to one another, using a single control element. The surgical retraction device may additionally comprise means for discretely varying the intensity of light illuminating a surgical area using the single control element. In an embodiment, the means for illuminating a surgical area may comprise a two-dimensional array of organic light-emitting diodes. In an embodiment, means for controlling placement of the illuminated surgical area along a first axis may comprise a cable linkage from the single control element to louvers placed proximate to the means for illuminating the surgical area. In an embodiment, the means for controlling placement of the illuminated area along a first axis may comprise a stepper motor which, responsive to movement of the single control element, may operate to modify the position of the louvers placed proximate to the means for illuminating the surgical area. In an embodiment, the stepper motor of the surgical retraction device may operate to adjust an angle of one or more louvers, of an array of louvers, with respect to a plane of a two-dimensional array of organic light-emitting diodes.

It should be understood that the aforementioned implementations are merely example implementations, and that claimed subject matter is not necessarily limited to any particular aspect of these example implementations.

BRIEF DESCRIPTION OF DRAWINGS

Claimed subject matter is particularly pointed out and distinctly claimed in the concluding portion of the specification. However, both as to organization and/or method of operation, together with objects, features, and/or advantages thereof, it may best be understood by reference to the following detailed description if read with the accompanying drawings in which:

Figure 1A:
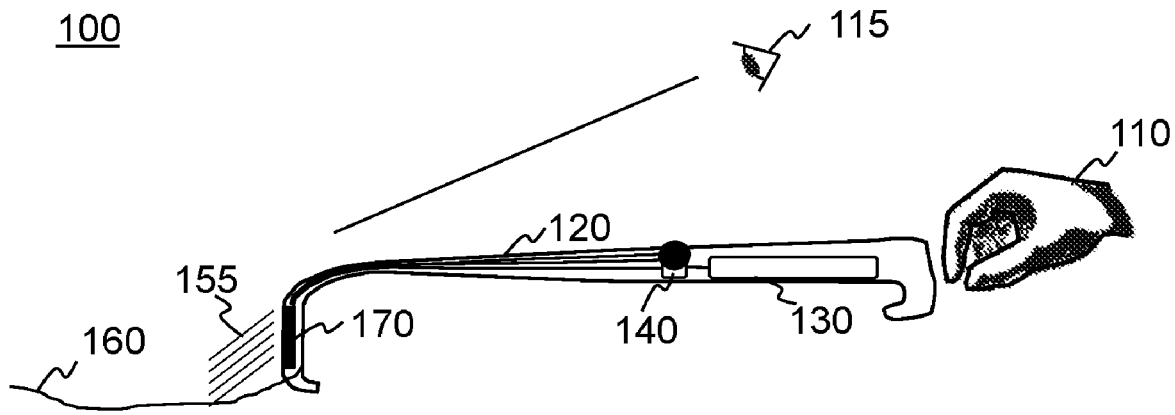
FIG. 1A is an illustration of a surgical retractor in use during a surgical procedure according to an embodiment.

Reference is made in the following detailed description to accompanying drawings, which form a part hereof, wherein like numerals may designate like parts throughout to indicate corresponding and/or analogous components. It will be appreciated that components illustrated in the figures have not necessarily been drawn to scale, such as for simplicity and/or clarity of illustration. For example, dimensions of some components may be exaggerated relative to other components. Further, it is to be understood that other embodiments may be utilized. Furthermore, structural and/or other changes may be made without departing from claimed subject matter. It should also be noted that directions and/or references, for example, up, down, top, bottom, and so on, may be used to facilitate discussion of drawings and/or are not intended to restrict application of claimed subject matter. Therefore, the following detailed description is not to be taken to limit claimed subject matter and/or equivalents.

DETAILED DESCRIPTION

Reference throughout this specification to "one example," "one feature," "one embodiment," "an example," "a feature," or "an embodiment" means that a particular feature, structure, or characteristic described in connection with the feature, example or embodiment is included in at least one feature, example or embodiment of claimed subject matter. Thus, appearances of the phrase "in one example," "an example," "in one feature," a feature," "an embodiment," or "in one embodiment" in various places throughout this specification are not necessarily all referring to the same feature, example, or embodiment. Furthermore, particular features, structures, or characteristics may be combined in one or more examples, features, or embodiments.

As previously described, a surgeon may utilize a surgical retractor to draw or pull away lateral and deep layers of tissue to expose one or more underlying features of, for example, a human or animal body. Retraction of lateral and deep layers may permit the surgeon and/or other medical personnel to perform surgical procedures, for example, deep within a human or animal body. However, on occasion, polished, sterilized surgical instruments, such as a retractor, may produce glare from overhead illumination sources. Responsive to observing such glare, a surgeon may be required to shift his or her position and/or reposition one or more surgical instruments. Such adjustment of a surgeon's position and/or repositioning of surgical instruments may reduce a surgeon's efficiency, for example, and may increase the time required to complete a surgical procedure, which may lead to potentially increased postoperative complications associated with prolonged operating times, for example, or may render a procedure more technically difficult.

In some instances, such as during very precise surgical procedures involving fine structures of the human body, an amount of overhead light illuminating a surgical area may be increased so as to permit the surgeon to clearly view the surgical area and to improve surgical safety by, for example, reducing surgeon error, such as inadvertently cutting, suturing, and/or inadvertently damaging vital anatomical structures. However, in these instances, and others, such an increase in ambient and/or overhead illumination may exacerbate glare produced by surgical instruments or create over illumination of the areas surrounding and external to the surgical incision. Presence of additional glare may, in turn, require additional repositioning of one or more surgical instruments, for example or dimming the lights below acceptable levels to reduce glare, for example.

In embodiments, use of an illuminating surgical retractor may reduce a need for ambient surgical lighting, such as overhead lighting, which may reduce or eliminate glare introduced by overhead and/or ambient surgical lighting as well as reducing shadowing effects. Such reduction, or elimination of glare entirely, may, for example, reduce annoying eye strain experienced by a surgeon, as well as reduce the need to reposition surgical instruments during surgical procedures, for example. Accordingly, embodiments may bring about a reduction in the time required to perform a surgical procedure as well as an increase in a surgeon's comfort and efficiency.

Accordingly, an illuminating surgical retractor may represent an approach toward reducing glare introduced by various overhead and/or ambient surgical lighting systems. In an example embodiment, an illuminating surgical retractor may comprise light emitting diodes (LEDs) and/or organic light-emitting diodes (OLEDs), which may serve to diffusely illuminate a surgical field without significant illumination of surrounding areas. In embodiments, an illuminating surgical retractor may comprise a single control element, positioned near a handle or a grip of the device, which may permit a surgeon to control intensity of light from, for example, light-emitting diodes. In one implementation, of which many are possible, a surgeon may adjust intensity of light from an illuminating surgical retractor by way of momentarily depressing the single control element. Momentarily depressing the single control element may adjust intensity of light in one of a plurality of incremental steps, such as five steps, 10 steps, 12 steps, and so forth. Such step light intensity may benefit a surgeon, and patient, by permitting the surgeon to precisely control intensity of light illuminating a surgical field.

In an embodiment, a single control element of an illuminating surgical retractor may be movable from side-to-side (e.g., left to right), which may control the side-to-side placement of illumination incident on a surgical field. Accordingly, a surgeon may be capable of easily modifying the direction, such as from side-to-side, of light illuminating the surgical field. In some embodiments, the single control element may additionally be movable in a second dimension, perpendicular to a side-to-side direction, which may modify the direction, such as toward the surgeon or away from the surgeon, of light illuminating the surgical field.

An illuminating surgical device incorporating a single control element may therefore permit a surgeon to control intensity of light illuminating a surgical field as well as to control side-to-side and front-to-back movement of light illuminating the surgical field. Thus, the surgeon may avoid the need to reposition his or her thumb or finger, for example, to manipulate the surgical device. This may permit a surgeon to remain focused on the surgical area of interest, avoiding the need to manipulate the surgical device using, for example, multiple fingers and/or a need to reposition one or more fingers on the surgical device without a need to manipulate controls of the surgical device. Use of single control element may assist in maintaining a sterile surgical environment by removing the need to encapsulate multiple control elements (e.g., separate controls for intensity, side-to-side movement, front-to-back movement, etc.).

In embodiments, illuminating elements, which may comprise approximately in the range of 15-30 LEDs, may be affixed in a two-dimensional array across a substrate layer. In particular embodiments, one or more LEDs may be staggered along a third dimension (e.g., depth) to bring about a three-dimensional array of LEDs. In particular embodiments, a two-dimensional or three-dimensional array of surface-mounted, side-firing LEDs, such as those obtained from the Nichia Corporation at 491 Oka, Kaminaka-Cho, Anan-Shi, TOKUSHIMA 774-8601, Japan, may be utilized. Illuminating elements may generate light comprising a color temperature of, for example, approximately in the range of 5000 degrees Kelvin to 7500 degrees Kelvin. In particular embodiments, illuminating elements may generate light comprising a lower color temperature, such as approximately in the range of 3500 degrees Kelvin, which may permit, for example, warming of tissue during a surgical procedure. In other embodiments illuminating elements may generate light outside of the visible wavelengths, such as infrared and/or ultraviolet wavelengths. It should be noted that a variety of LEDs may be utilized and claimed subject matter is not limited to any particular type of LED or type of LED technology.

As will be described in greater detail herein, illuminating elements, such as LEDs, may be arranged anharmonically in a manner that reduces or eliminates a possibility of noticeable and destructive interference or the over focusing of individual LED elements in the surgical field. Responsive to anharmonic spacing of LED illuminating elements, an illumination area may appear diffuse and uniformly illuminated without significant variation in light hue, color, intensity, for example. Anharmonic spacing of illuminating elements may give rise to additional benefits, and claimed subject matter is not limited in this respect.

In embodiments, a spacing layer may be disposed atop a substrate layer comprising an array of two-dimensional illuminating elements, such as LEDs. However, in some embodiments, LEDs may be staggered in a third dimension, such as depth. A spacing layer may comprise a two-dimensional array of orifices, each of which, for example, may accommodate a corresponding illuminating element of an array of two-dimensional illuminating elements. A spacing layer may additionally accommodate a two-dimensional array of reflective surfaces, which may serve to direct light from illuminating elements in an approximately upward direction away from a substrate layer.

In embodiments, a louvered layer may be disposed atop a spacing layer, which may serve to direct light from a reflective surface, for example, towards a surgical field. A louvered layer may include a two-dimensional array of individual louvers oriented at angles approximately in the range of 120 degrees to 150 degrees relative to a substantially planar horizontal surface. However, it should be noted that embodiments of claimed subject matter may embrace louvers comprising differing orientations with respect to a blade surface, such as angular orientations of less than 120 degrees and angular orientations of greater than 150 degrees, for example. In embodiments, a louvered layer may reduce backscatter, thereby confining an illumination area to encompass a surgical field.

In embodiments, one or more substrate layers, one or more spacing layers, one or more reflective layers, and one or more louvered layers may be constructed so as to form a blade, which may then be encapsulated utilizing a transparent, fluid resistant (e.g., hydrophobic) encapsulant. A transparent encapsulant, as well as reflective layers, louvered layers, and so forth may permit substantially lossless transmission of illumination from illuminating elements. In a particular embodiment, a transparent encapsulant may have intermixed particles which may homogenize light, homogenize a color temperature, and/or provide diffusion of light for example. Such an encapsulant may, for example, include a photo luminescent phosphor, such as cerium-doped yttrium aluminum garnet (CE:YAG) or optically transparent particles comprising a differing refractive index and a matrix of such as $TiO_2$, $SiO_2$, or ZnO, or any combination thereof, for example.

In particular embodiments, many chromophores are possible such as quantum dot particles, which may gain popularity four application in liquid crystal displays. In embodiments, particles small enough to raise an overall refractive index of the matrix (such as less than approximately 30 nm or smaller) may be utilized. Larger particles, such as those greater than approximately 30 nm may not exhibit Rayleigh scattering but may, in some embodiments, exhibit Mie scattering. Such scattering may result in opaque matrices with increased diffuse transmissions, which may bring about a reduction in specular transmittance, for example. In an embodiment, $TiO_2$ particles comprising a radius approximately in the range of 200 nm to 250 nm, for example, comprising an index of refraction approximately in the range of 2.4-2.6, for example, may be utilized as a scatter matrix. In embodiments, zirconia may also be utilized. Although in some embodiments, silica may be added to higher refractive index matrices to reduce a refractive index.

FIG. 1A is an illustration of a surgical retractor in use during a surgical procedure according to an embodiment 100. As shown in FIG. 1A, surgeon's hand 110 may be utilized to operate surgical retractor 120, such as during a surgical procedure, for example, to draw or retract one or more layers of tissue, for example. Responsive to retraction of lateral and deep layers of tissue, for example, using blade portion 170, surgical field 160 may be exposed, for example, to be viewed by a surgeon, represented by eye 115. In the embodiment of FIG. 1A, manipulation of single control element 140 may permit a surgeon, for example, to manipulate intensity of illumination 155 incident on surgical field 160. In addition, manipulation of single control element 140 may permit a surgeon to control side-to-side movement (e.g., into and out of the page) of the illumination of surgical field 160 as well as to control the front-to-back movement (e.g., in directions to and away from surgeon's hand 110) of the illumination incident on surgical field 160. In the embodiment of FIG. 1A, surgical retractor 120 may comprise battery 130, which may be disposed in a rear volume of the device such as beneath an area gripped by surgeon's hand 110.

Figure 1B:
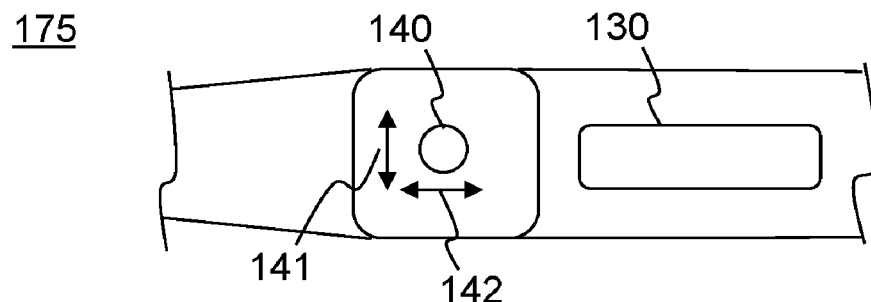
FIG. 1B is an illustration of a portion of the surgical retractor of FIG. 1A according to an embodiment.

FIG. 1B is an illustration of a portion of the surgical retractor of FIG. 1A according to an embodiment 175. In FIG. 1B, single control element 140 comprises a circular shape, but may comprise any other suitable shape, and claimed subject matter is not limited in this respect. For example, single control element may comprise an elliptical or oval shape, a substantially square shape, or a shape that may at least roughly accord with a portion of a thumb, knuckle, or forefinger, for example, of surgeon's hand 110 of FIG. 1A, for example.

In particular embodiments, single control element 140 may be movable in one or more directions to permit movement of illumination 155, which may illuminate surgical field 160. For example, movement of single control element 140 along a first axis, such as side-to-side direction 141, may bring about movement of illumination 155 along an axis parallel, for example, to side-to-side direction 141. In one example implementation, a slight movement or nudge of single control element 140 to the right side may slowly move illumination 155 towards the right side of surgical field 160, for example. Likewise, a slight movement of single control element 140 to the left side may slowly move illumination 155 towards the left side of the surgical field 160. In embodiments, a larger displacement of single control element 140 to the right or to the left may bring about more rapid movement of illumination 155 towards a corresponding side of surgical field 160.

In certain embodiments, single control element 140, positioned in front of battery 130, may be additionally movable along a second axis, such as front-to-back direction 142, which may bring about movement of illumination 155 along an axis parallel, for example, to front-to-back direction 142. In embodiments, the first and second axes may be parallel to one another, although claimed subject matter is not limited in this respect. Rather, claimed subject matter is intended to embrace all single control elements, which may bring about control over illumination of the surgical field in a two-dimensional plane. In one example implementation, a slight forward movement or nudge of single control element along front-to-back direction 142 may slowly move illumination 155 towards a portion surgical field 160 away from surgeon's hand 110. Likewise, a slight movement or nudge of single control element in opposite direction may slowly move illumination 155 towards a portion of surgical field 160 more proximate to surgeon's hand 110. In embodiments, a larger displacement of single control element 140 in forward or rearward directions may bring about more rapid movement of illumination 155 towards a corresponding portion of surgical field 160.

In the embodiment of FIG. 1B, depressing single control element 140 may permit stepped or incremental control over intensity of light emanating from blade 170 of, for example, blade 170 of a surgical retractor. For example, depressing single control element 140 a first time may bring about illumination at a first increment, step, or level. Depressing single control element 140 a second time may bring about illumination at a second increment, step, or level. In embodiments, depressing a single control element an additional number of times may bring about additional stepping or incrementing of illumination, for example, from a low level of illumination to a high level of illumination. Upon achieving a high level of illumination, depressing a single control element one or more additional times may return illumination to a low level of illumination.

In particular embodiments, depressing and sustaining single control element 140 in a depressed position may bring about increased illumination without, for example, depressing single control element 140 additional times. At times, a "press and hold" feature, in which holding single control element 140 in a depressed position to bring about incremental increases in illumination intensity may permit a surgeon to hold a surgical retractor in a steady, fixed position while adjusting illumination intensity.

Figure 2:
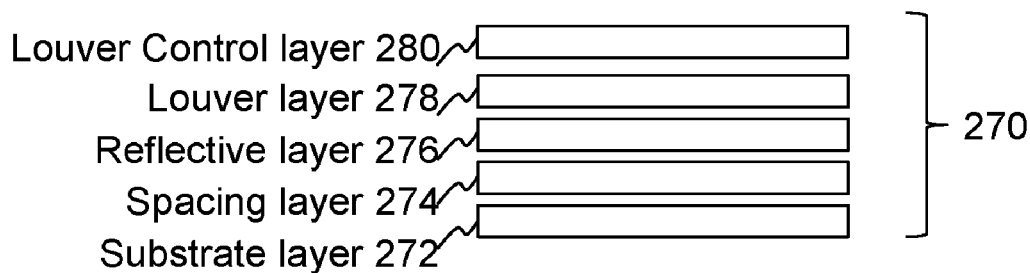
FIG. 2 is a diagram showing a general scheme toward constructing an illuminating surgical device according to an embodiment.

FIG. 2 is a diagram showing a general scheme toward constructing a blade portion of an illuminating surgical device according to an embodiment 200. As shown in FIG. 2, blade portion 270, which may be rotated 90 degrees clockwise from its orientation in FIG. 1A (170), is shown as comprising substrate layer 272, spacing layer 274, reflective layer 276, louver layer 278, and louver control layer 279. Blade portion 270 may comprise additional layers not shown in FIG. 2, and claimed subject matter is not limited in this respect. After assembly of substrate, spacing, reflective, louver, and louver control layers, blade portion 270 may be encapsulated using a transparent hydrophobic encapsulant that may resist materials, such as water-based materials, that may come into contact with an illuminating surgical device. A transparent hydrophobic encapsulant may protect against, for example, fluids from surgical area 160, cleaning solvents and surfactants, and so forth. Transparent encapsulants may be utilized to protect illuminating surgical device 120 from additional fluids and/or materials, and claimed subject matter is not limited in this respect.

Figure 3:
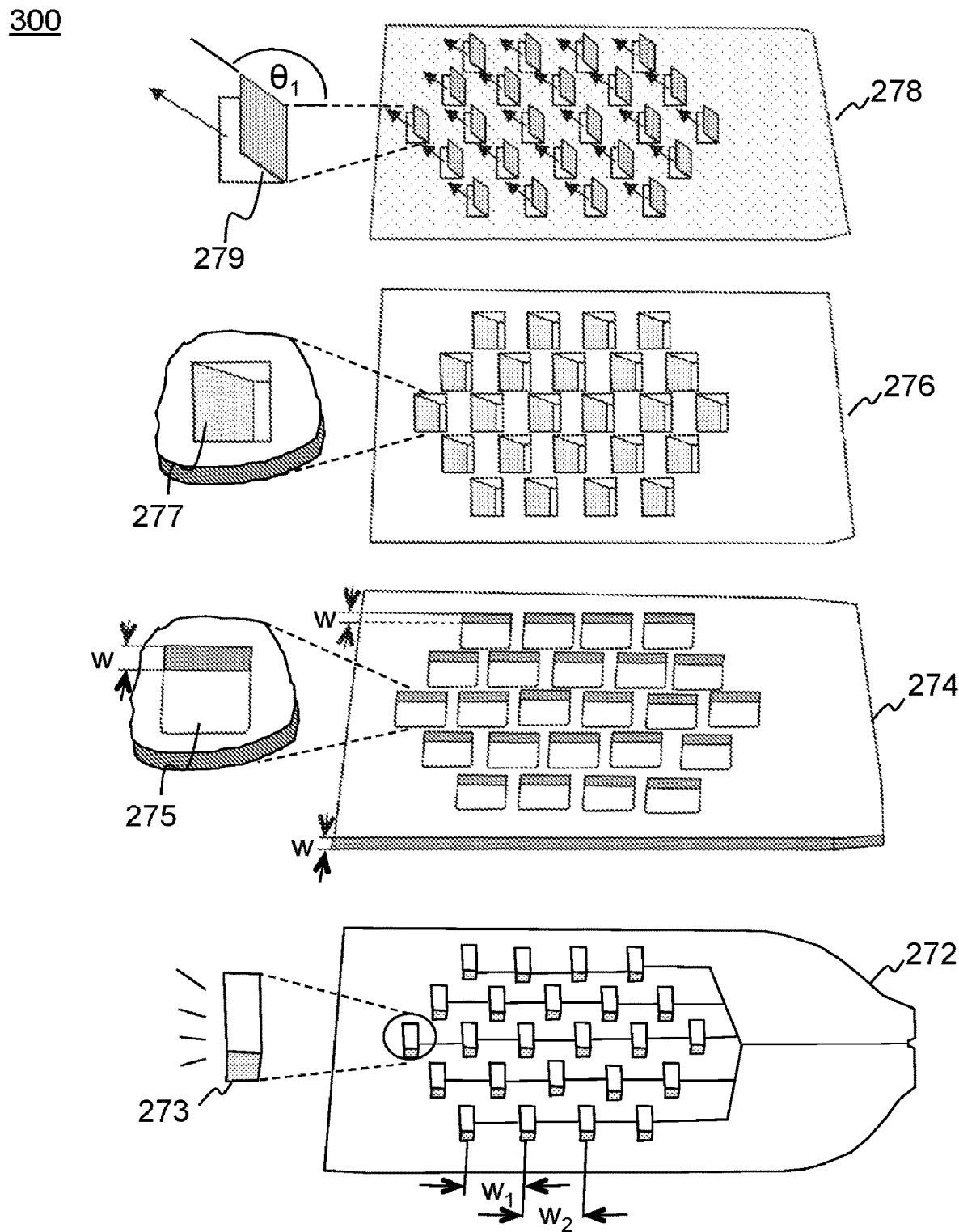
FIG. 3 is an illustration showing details of the construction of a substrate, spacing, reflective, and louver layer of an illuminating surgical device according to an embodiment.

FIG. 3 is an illustration showing details of the construction of a substrate, spacing, reflective, and louver layer of an illuminating surgical device according to an embodiment 300. Beginning near a bottom portion of FIG. 3, substrate layer 272 may comprise an array, such as a two-dimensional array, of illuminating elements 273. In an embodiment, illuminating elements 273 may comprise side-firing LEDs, which may generate illumination that emanates predominantly from a side, such as the left-hand side, as shown in FIG. 3. However, it should be noted that claimed subject matter is intended to embrace a variety of illumination sources, such as side firing LEDs, end-firing LEDs, and other LED types, without limitation.

As shown in FIG. 3, certain adjacent pairs of illuminating elements 273 of an array of illuminating elements may be separated by a distance of, for example, $w_1$, and certain other adjacent pairs of illuminating elements 273 may be separated from one another by a distance of, for example, $w_2$. In embodiments, $w_2$ may be greater than $w_1$, although other embodiments may employ differing spacings, such as, for example, spacings in which $w_1$ may be greater than $w_2$, for example, and claimed subject matter is not limited in this respect. In embodiments, such anharmonic and perhaps three-dimensional spacing (in which certain LEDs disposed atop a substrate layer 272 may be recessed with respect to one another) may be utilized to reduce, or to eliminate, constructive and/or destructive interference brought about by harmonic spacing of illuminating elements 273. In the embodiment of FIG. 4, illuminating elements 273 may be arranged to prevent, for example, occurrence of $n_1\lambda=n_2\lambda$, in an illumination area, which may give rise to "banding," or other noticeable areas of non-uniform intensity which may occur within the illumination area. To reduce the possibility of banding and/or other nonuniform illumination of an area, inter-element spacing ($w_1$) between a first pair of adjacent illuminating elements, which may be represented by $n_1\lambda$ may be made unequal to inter-element spacing ($w_2$) between a second pair of adjacent illuminating elements, which may be represented by $n_2\lambda$. It should be noted, however, that claimed subject matter is not limited to any particular approach toward reducing nonuniform illumination. For example, some embodiments may utilize one or more light diffusers, one or more homogenizers, etc., and claimed subject matter is not limited in this respect. Additionally, in particular embodiments, LEDs of different color temperature and/or wavelength may provide intentional non-uniform illumination, for example.

Spacing layer 274, shown as having width "w" in FIG. 3, may comprise orifices 275, which may be machined into a solid material. In an embodiment, orifices 275 may be arranged in an array so as to be placed atop substrate layer 272. In particular embodiments, illuminating elements 273 may fit within a corresponding orifice. Reflective layer 276, comprising an array of reflectors 277, may be placed atop spacing layer 274 so as to reflect light emanating from illuminating elements 273. In embodiments, reflectors 277 may be sloped downwardly from the plane of the reflective layer so as to fit within orifices 275 of spacing layer 276. In an embodiment, spacing layer 274 and reflective layer 276 may be provided as a single layer comprising injection-molded plastic and may utilize a metal-plated reflective surface.

Louver layer 278 may be affixed atop reflective layer 276, which may direct light reflected from reflectors 277 toward, for example, surgical area 160 of FIG. 1A. As shown in FIG. 3, louvers 279 may be adjustable, for example, from an orientation of approximately a 135 degree angle ($\theta_1$) relative to the plane of louver layer 278 up to an angle to approach 165 degrees, 170 degrees, or 175 degrees for example relative to louver layer 278. Of course, louvers 279 may be adjustable to an orientation approaching 180 degrees with respect to louver layer 278, which may, for example, nearly completely occlude orifices 275 so as to permit very little light to illuminate, for example, surgical area 160 of FIG. 1A. It should be noted that, claimed subject matter may embrace louvers adjustable at a variety of angles, such as angles less than 135 degrees (e.g., 95 degrees, 105 degrees, 110 degrees, 115 degrees, etc.) with respect to the plane of louver layer 278.

Figure 4A:
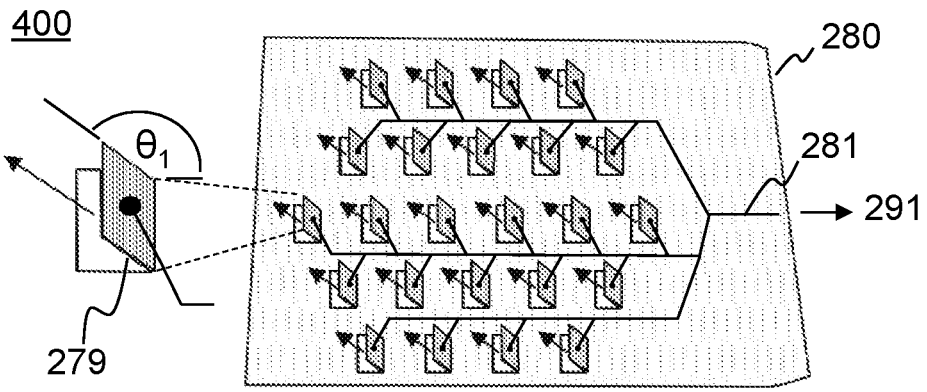
FIGS. 4A and 4B are illustrations showing details of the construction of a louver control layer of an illuminated surgical device according to an embodiment.
Figure 4B:
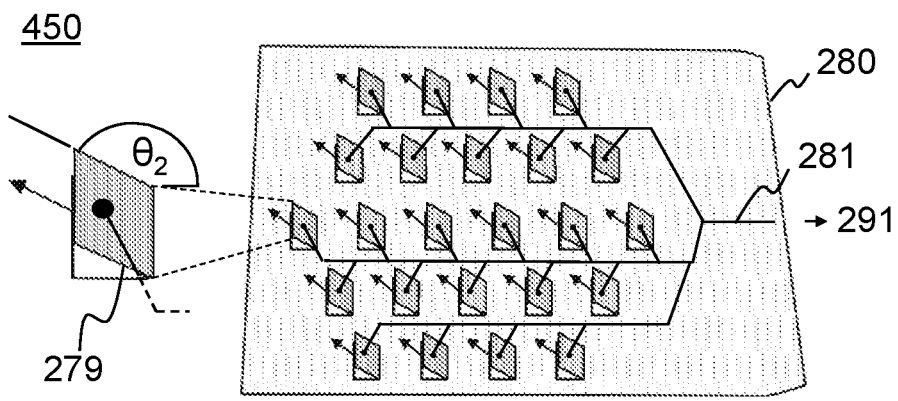

FIGS. 4A and 4B are illustrations showing details of the construction of a louver control layer of an illuminating surgical device according to embodiments 400 and 450. In FIG. 4A (embodiment 400) louver control layer 280 is shown as incorporating mechanical linkage 281, which may comprise a Bowden cable, for example, which may branch to a plurality of secondary and tertiary mechanical linkages, which may be utilized to draw one or more of louvers 279 from a relatively closed position to a relatively open position. In embodiments, louvers 279 may be biased, such as by way of a spring or other type of tensioner, to a closed position so as to provide cover to orifices 275. In embodiments, such biasing of louvers 279 to a closed position may preclude orifices 275 from gathering airborne contaminants, such as dust, for example, or fluid borne contaminants, when the surgical device is not in use. Biasing of louvers 279 to a closed position may bring about additional benefits, and claimed subject matter is not limited in this respect.

In embodiments, responsive to tension in the direction of arrow 291, mechanical linkage 281 along with secondary and tertiary mechanical linkages may draw louvers 279 from a substantially closed state to an substantially open state, as well as partially-open states between a substantially closed at a substantially open state, which may permit illumination of a surgical field, such as surgical field 160 of FIG. 1A. In embodiments 400 and 450, mechanical linkage 281 may couple to single control element 140. Thus, in one implementation, rearward movement of single control element 140 along front-to-back direction 142 may bring about tension in the direction of arrow 291, thereby at least partially opening one or more of louvers 279.

In embodiments, as tension in the direction of arrow 291 is increased, louvers 279 may gradually open from a position that permits only minimal illumination of the surgical field, for example, to a position that permits increasing illumination of the surgical field. Thus, for example, as shown in FIG. 4A (embodiment 400), a first level of tension in the direction of arrow 291 may open one or more of louvers 279 so as to form an angle $\theta_1$ relative to a plane of louver control layer 280. Likewise, as shown in FIG. 4B (embodiment 450) a second level of tension, which may be indicated by a somewhat smaller arrow in the direction of 291 may open one or more of louvers 279 so as to form an angle $\theta_2$ relative to the plane of control layer 280. Thus, as shown in FIGS. 4A and 4B, tension conveyed from mechanical linkage 281, along secondary and tertiary mechanical linkages, may operate to control a decree to which louvers 279 open and close, which may permit an adjustment in illumination that emanates from an illuminating surgical device.

It should be noted that although FIGS. 4A and 4B have been described incorporating mechanical linkage 281, alternative embodiments may utilize different approaches toward modulating, controlling, or adjusting the light generated by, for example, illuminating elements 273 to illuminate a surgical field. Accordingly, claimed subject matter is intended to embrace all such techniques and approaches toward providing controllable illumination of the surgical field. For example, in an embodiment with reference to FIG. 7, one or more stepper motors may be used to provide tension on mechanical linkage 281.

Figure 5:
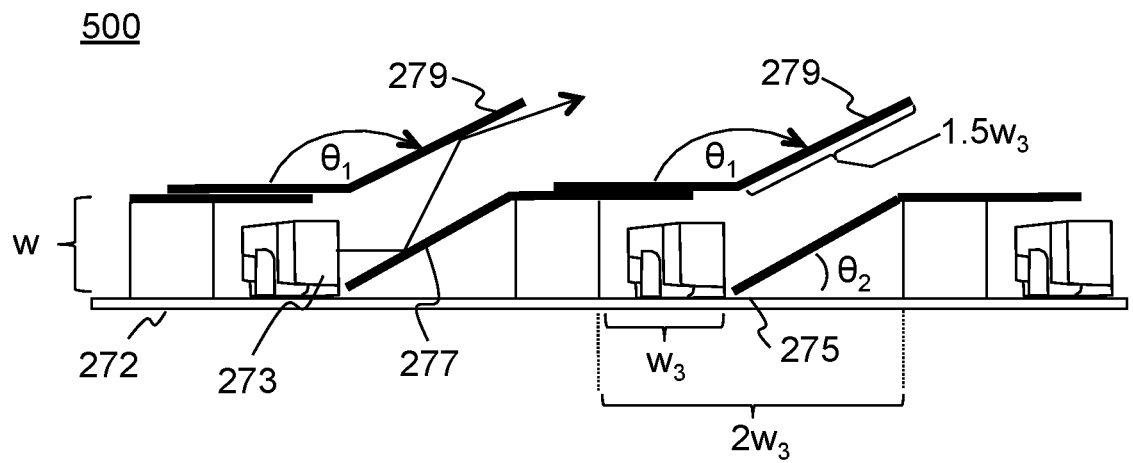
FIG. 5 is an illustration showing integration of individual portions of the illuminating surgical device of FIGS. 3, 4A, and 4B according to an embodiment.

FIG. 5 is a side view showing details of layers of the illuminating surgical device of FIGS. 3, 4A, and 4B according to an embodiment 500. In FIG. 5, illuminating elements 273 are shown mounted atop substrate layer 272. Although illuminating elements 273 may be illustrated as comprising side-firing LEDs, claimed subject matter is intended to embrace any light-generating device that may be mounted atop a substrate layer and fitted within an orifice, such as orifice 275. Illuminating element 273 is shown adjacent to a wall having a height w, which may correspond to a thickness dimension of spacing layer 274 of FIG. 3. Thus, while disposed within the confines of orifice 275, luminous energy generated by illuminating elements 273 may impinge upon reflectors 277 and the undersides of louvers 279 towards an illumination area.

In embodiments, reflectors 277 may be oriented at an angle $\theta_2$, which may be selected to increase illumination of a target illumination area, such as a surgical field, for example, without a significant backscatter from the top sides of adjacent ones of louvers 279. It is contemplated that $\theta_2$ may comprise a value approximately in the range of 30 degrees and 50 degrees, although in particular embodiments, $\theta_2$ may comprise values less than 30 degrees (e.g., 25 degrees, 20 degrees, and so forth) or may comprise values greater than 50 degrees (e.g., 55 degrees, 60 degrees, and so forth) and claimed subject matter is not limited in this respect. FIG. 5 additionally indicates a horizontal dimension of $w_3$, which corresponds to a horizontal dimension of illuminating elements 273 mounted atop substrate layer 272.

In the embodiment of FIG. 5, the horizontal dimension of orifice 275 ($2w_3$), which may be formed within spacing layer 274 of FIG. 3, for example, is shown as comprising twice the horizontal dimension of illuminating element 273 ($w_3$). FIG. 5 additionally indicates a linear dimension of louvers 279 as being approximately 1.5 times the horizontal dimension of illuminating elements 273 ($1.5w_3$). However, selection of a linear dimension of louvers 279, such as, for example, a linear dimension of 1.5 times the horizontal dimension of illuminating elements 273 may be selected according to an individual application. Thus, again, the relative dimensions of illuminating element 273, orifice 275, louver 279, and so forth, are provided as an illustrative embodiment, and claimed subject matter is not limited in this respect.

Figure 6:
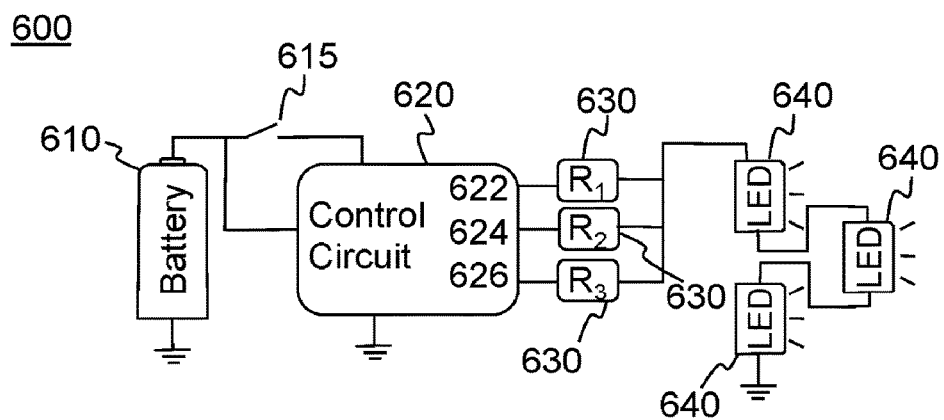
FIG. 6 is a schematic diagram for a circuit utilized in an illuminating surgical device according to an embodiment.

FIG. 6 is a schematic diagram for a circuit utilized in an illuminating surgical device according to an embodiment 600. In the embodiment of FIG. 6, battery 610 and may represent any type of chemical energy storage unit capable of providing sufficient voltage and current to operate control circuit 620, and LEDs 640, by way of current-limiting resistors 630. In an embodiment, switch 615, may operate in conjunction with control circuit 620 to provide a stepped level of control of the illumination provided by LEDs 640. In particular embodiments, control circuit 620 may correspond to a single control element, such as single control element 140, for example, of FIG. 1A. Additionally, LEDs 640 may correspond, for example, to illuminating elements 273 of FIG. 3. Thus, in certain embodiments, depressing switch 615 for a brief period may give rise to control circuit 620 supplying or generating an electrical current, which may flow through output port 622 and through LEDs 640, thereby providing illumination at a first level. In an embodiment, the first illumination level may correspond to a relatively low level of illumination.

In an embodiment, depressing switch 615 for a second brief period may give rise to control circuit 620 supplying or generating a second electrical current, which may flow through output port 624 and through LEDs 640, thereby providing illumination at a second level. In an embodiment, the second illumination level may correspond to a higher level of illumination than the first illumination level. Likewise, depressing switch 615 for third brief period may give rise to control circuit 620 supplying or generating a third electrical current, which may flow through output port 626 and through LEDs 640, thereby providing illumination at a third level. Accordingly, as may be appreciated, successive momentary closures of switch 615 may give rise to control circuit 620 supplying current to one or more of output ports 622, 624, and 626. Although claimed subject matter is not limited in this respect, Table I (below) illustrates one possible mapping of switch closures versus current signals present at one or more output ports of control circuit 620:

TABLE I

| Switch Closure (615) | Current at Signal Port(s) |
|---|---|
| 1 | 622 |
| 2 | 624 |
| 3 | 626 |
| 4 | 622, 624 |
| 5 | 622, 626 |
| 6 | 624, 626 |
| 7 | 622, 624, 626 |
| 8 | None |

Accordingly, from Table I, it can be seen that seven momentary closures of switch 615 may result in a corresponding number of current levels present at one or more of output ports 622, 624, and a 626 of control circuit 620. Further, in an embodiment, and eighth momentary closure of switch 615 may return current levels present at output ports 622, 624, and 626 of control circuit 620 to a substantially inactive state (approximately 0.0 mA). After returning control circuit 620 to an inactive state, successive switch closures may, again, bring about a presence of current at one or more of output ports 622, 624, and/or 626, for example. It should be noted that although the example of FIG. 6 describes a control circuit having three outputs, which may give rise to seven levels of illumination, claimed subject matter is not limited in this respect. Rather, claimed subject matter is intended to embrace control circuits, such as control circuit 620, which may provide a smaller number of output ports at which current may be supplied, such as two output ports or fewer, or may provide a larger number of output ports at which current may be supplied, such as five output ports, seven output ports, 10 output ports and so forth.

In a particular embodiment of an illuminated surgical device and control element, a Texas Instruments MSP430G microcontroller (available from Texas Instruments Incorporated having offices at 12500 TI Boulevard, Dallas, Tex. 75243 USA) may be utilized. In one possible embodiment, a microcontroller may be programmed so as to permit a single control element, such as a single mechanical non-toggling switch, to transmit a trigger signal to the controller to step to the next illumination level, such as described hereinabove. In an embodiment, use of a microcontroller such as the MSP430G may comprise a "sleep" mode, in which the microcontroller is powered to an inactive state, without human intervention, by allowing the device to rest or to remain undisturbed for a selectable period of time such as approximately 5 min., approximately 10 min., or other suitable time period, for example. While in an inactive state, the device may extinguish illumination emanating from illuminating elements, such as illuminating elements 273.

Figure 7:
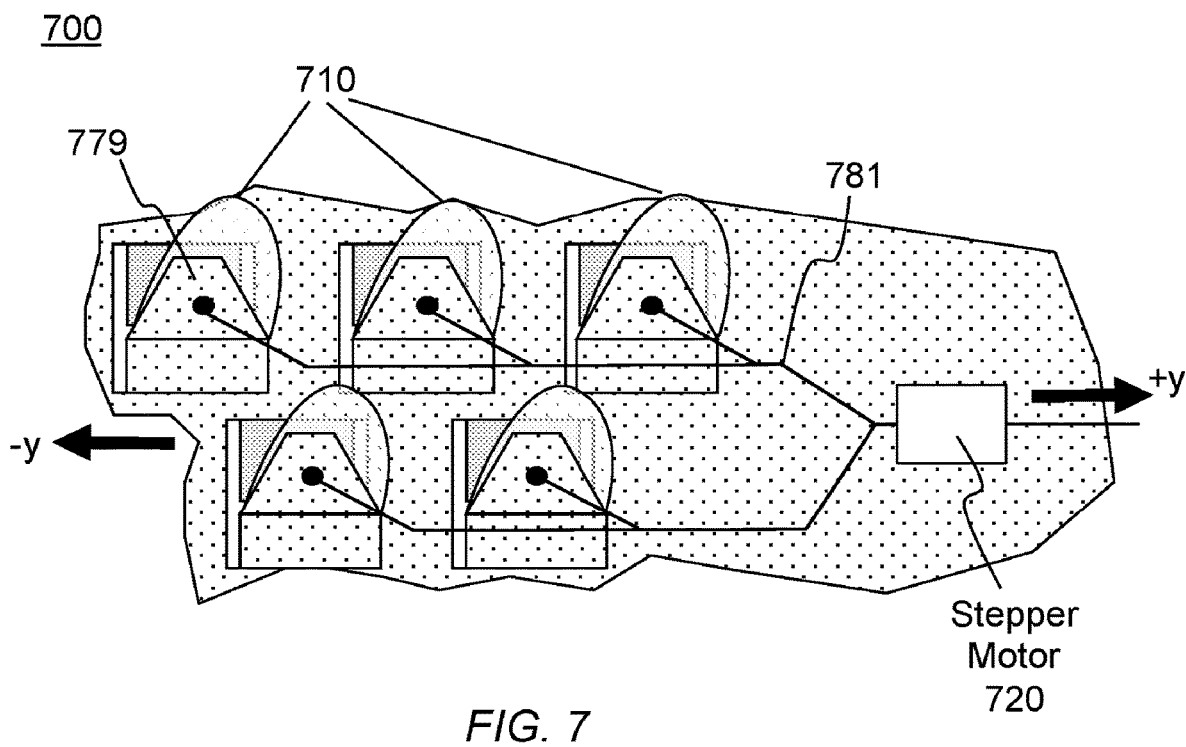
FIG. 7 shows a portion of an array of louvers of an illuminated surgical retractor, which may be controllable to permit illumination to be controlled from side-to-side according to an embodiment.

FIG. 7 shows a portion of an array of louvers of an illuminated surgical retractor, which may be controllable to permit illumination to be controlled from side-to-side according to an embodiment 700. In the embodiment of FIG. 7, mechanical linkage 781 may be controlled by stepper motor 720. Responsive to side-to-side movement of a single control element, such as single control element 140, stepper motor 720 may draw louvers 779 in a +y direction. In an embodiment, movement of louvers 779 in a +y direction may give rise to illumination beams 710 shifting in a corresponding (+y) direction. Of course, in lieu of stepper motor 720, louvers 779 could be controlled via a Bowden cable, such as previously described in reference to FIG. 4A to control mechanical linkage 281. In a manner similar to the biasing of louvers 279 to a relatively closed position, louvers 779 may be biased so that illumination beams are directed in a slightly leftward (−y) so that stepper motor 720 need only provide tension in a +y direction in order to bring about movement of one or more of illumination beams 710.

While there has been illustrated and/or described what are presently considered to be example features, it will be understood by those skilled in the relevant art that various other modifications may be made and/or equivalents may be substituted, without departing from claimed subject matter. Additionally, many modifications may be made to adapt a particular situation to the teachings of claimed subject matter without departing from the central concept(s) described herein. Therefore, it is intended that claimed subject matter not be limited to the particular examples disclosed, but that such claimed subject matter may also include all aspects falling within appended claims and/or equivalents thereof.

The terms, "and", "or", and "and/or" as used herein may include a variety of meanings that also are expected to depend at least in part upon the context in which such terms are used. Typically, "or" if used to associate a list, such as A, B or C, is intended to mean A, B, and C, here used in the inclusive sense, as well as A, B or C, here used in the exclusive sense. In addition, the term "one or more" as used herein may be used to describe any feature, structure, and/or characteristic in the singular and/or may be used to describe a plurality or some other combination of features, structures and/or characteristics. Though, it should be noted that this is merely an illustrative example and claimed subject matter is not limited to this example.

What is claimed is:

1. A surgical retraction device, comprising:
   means for illuminating a surgical area;
   means for controlling one or more louvers proximate to the means for illuminating the surgical area to control placement of the illuminated surgical area along a first axis and a second axis substantially perpendicular to one another; and
   means for stepping, in discrete steps, the intensity of the illumination of the surgical area using a single control element to control electric current delivered to the means for illuminating the surgical area.

2. The surgical retraction device of claim 1, wherein the means for controlling placement of the illuminated surgical area along the first axis comprises a stepper motor to operate to modify the position of the one or more louvers responsive to the movement of the single control element.

3. The surgical retraction device of claim 2, wherein the stepper motor operates to adjust an angle of the one or more louvers of an array of louvers, with respect to a plane of a two-dimensional array of organic light-emitting diodes.

4. An illuminating surgical device, comprising:
   a two-dimensional array of illuminating elements to direct light toward a surgical field; and
   a single control element, to control intensity of light from the two-dimensional array of illuminating elements responsive to pressing the single control element, and movable along a first axis to control at least one louver to control the direction of the light within the surgical field from the two-dimensional array of illuminating elements in a direction parallel to the first axis, wherein the single control element is coupled to one or more switches, closure of the one or more switches to supply a signal to one or more illuminating elements of the two-dimensional array of illuminating elements.

5. The illuminating surgical device of claim 4, wherein the single control element is movable along a second axis substantially perpendicular to the first axis to control the direction of the light from the two-dimensional array of illuminating elements in a direction parallel to the second axis.

6. The illuminating surgical device of claim 4, wherein the pressing of the single control element is followed by releasing the single control element.

7. The illuminating surgical device of claim 4, wherein the single control element is configured to incrementally change intensity of the light from the two-dimensional array of illuminating elements responsive to a corresponding number of presses of the single control element.

8. The illuminating surgical device of claim 4, wherein the single control element is configured to incrementally change intensity of the light from the two-dimensional array of illuminating elements responsive to pressing and holding the single control element in place.

9. The illuminating surgical device of claim 4, further comprising a circuit to extinguish the illuminating surgical device based, at least in part, on inactivity of the illuminating surgical device over a duration.

10. The illuminating surgical device of claim 4, wherein the two-dimensional array of illuminating elements comprise organic light-emitting diodes (OLEDs).

\* \* \* \* \*